United States Patent [19]
Clark et al.

[11] Patent Number: 5,393,302
[45] Date of Patent: Feb. 28, 1995

[54] PROCESS FOR ENDOSTEAL LIGAMENT MOUNTING

[76] Inventors: Ron Clark, 676 S. Bluff, #205, St. George, Utah 84770; Raymond E. Olsen, 190 Summet Dr., Smithfield, Utah 84335; E. Marlowe Goble, 850 E. 1200 north, Logan, Utah 84321

[21] Appl. No.: 74,542

[22] Filed: Jun. 11, 1993

Related U.S. Application Data

[62] Division of Ser. No. 956,322, Oct. 5, 1992, Pat. No. 5,266,075.

[51] Int. Cl.⁶ .............................................. A61F 2/08
[52] U.S. Cl. ......................................... 623/13; 623/66
[58] Field of Search ...................... 623/15, 16, 66, 18

[56] References Cited

U.S. PATENT DOCUMENTS

| | | |
|---|---|---|
| 4,744,793 | 5/1988 | Parr et al. . |
| 4,772,286 | 9/1988 | Goble et al. . |
| 4,927,421 | 5/1990 | Goble et al. . |
| 4,950,270 | 8/1990 | Bowman et al. . |
| 5,129,902 | 7/1992 | Goble et al. . |
| 5,147,362 | 9/1992 | Goble . |

Primary Examiner—David J. Isabella
Attorney, Agent, or Firm—M. Reid Russell

[57] ABSTRACT

A process that utilizes a tendon threader for positioning and endosteally mounting a tendon within the endosteum of a closed tunnel end of a straight ligament tunnel that has been formed in a patient's knee in an arthroscopic surgical procedure for replacement of a cruciate ligament. The preferred tendon threader for use in a practice of the process includes a straight tubular body, with a handle arranged on one end, and the other tube end includes a pair of aligned wide longitudinal slots formed, with tube end remainder portions adjacent to which wide longitudinal slots each having a small longitudinal slot formed therein, the small slots for receiving a tendon, or a suture sewn onto the end of a tendon, fitted therein, forming a loop across the tube end. In a practice of the process the tendon threader is inserted into the straight ligament tunnel to where the tendon or suture loop is proximate to a ligament tunnel section end. Which procedure may be observed on a fluoroscopic monitor or utilizing an arthroscope fitted in the tendon threader tubular body. Whereat, a surgeon turns a pin into the side of the patient's knee, that travels through the ligament tunnel section and through the tendon or suture loop. The tendon threader is then removed leaving the tendon or suture folded over the pin, which tendon or suture end is then pulled over the pin to where the tendon ends are positioned over one another for mounting, under tension, as by stapling, onto the bone cortex surface adjacent to the straight ligament open tunnel end, completing the ligament mounting.

6 Claims, 3 Drawing Sheets

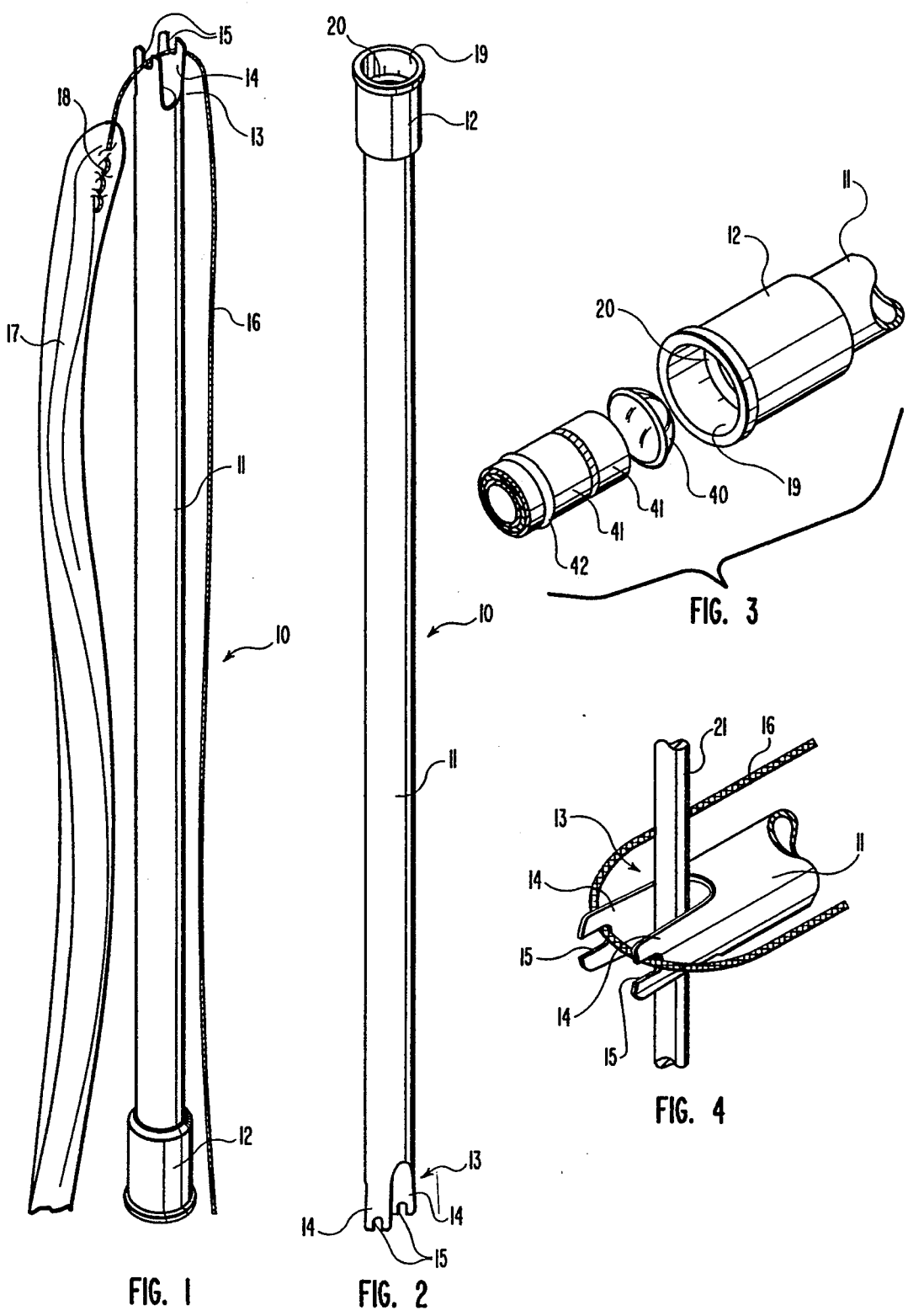

PROCESS FOR ENDOSTEAL LIGAMENT MOUNTING

This is a divisional application of U.S. patent application Ser. No. 07/956,322, filed Oct. 5, 1992, that resulted in a U.S. Pat. No. 5,266,075, issued Nov. 30, 1993.

BACKGROUND OF THE INVENTION

1. Field of the Invention

This invention relates to devices and procedures for their use in an arthroscopic surgical procedure for replacement of a knee cruciate ligament.

2. Prior Art

The present invention is in a device and its use for conveniently threading and mounting a tendon, or the like, into a closed femoral section of a straight ligament tunnel, that has been formed through the tibia and ligament points of origin and into the femur endosteum, for replacing a knee anterior cruciate ligament. Recently, in the field of arthroscopic surgery, for replacement of a knee anterior cruciate ligament, a procedure has been developed that, with the knee bent appropriately, involves forming a straight tunnel through the tibial tuberosity, across the anterior cruciate points of origin on the proximal tibia and distal femur surfaces, and into the femur endosteum. An end of a replacement ligament, either natural or prosthetic, is then fitted through the tibial opening and along the tunnel for seating in the femur endosteum. Some examples of which straight tunnel formation procedures and connectors for endosteally mounting a ligament end in the tunnel femur end section are shown in patents to Goble, et al, U.S. Pat. Nos. 4,772,286, 5,129,902, and 5,147,362. None of which procedures or devices, however, involves fitting a straight tube mounting a tendon into the closed femur section of a straight ligament tunnel and a procedure for mounting that tendon therein, like that of the invention.

The tendon threader of the invention is used to position a tendon in a femur tunnel section of a straight ligament tunnel. Once so positioned the tendon can be maintained therein by fitting a pin through the femoral tunnel and through the tendon threader with a tendon fitted thereover, forming a loop. The pin, as visualized arthroscopically looking through the tendon threader tubular body or on a fluoroscopic monitor, is fitted through the tendon loop, capturing it as a permanent tendon mounting. The tendon can then be drawn over the pin to where the ends are aligned. The aligned tendon ends can then be mounted, as by stapling them onto the bone surface, adjacent to the open tibial tunnel end. Heretofore, maintaining a ligament, tendon, or the like, in a closed ligament tunnel end, has required a connector device like those described in the above set out patents. Or an interference type device was fitted into the tunnel section, urging the tendon against the tunnel surface, locking it in place. An example of such an interference device is shown in a patent to Parr, et al, U.S. Pat. No. 4,744,793; with interference screws shown in patents to Goble, et al, U.S. Pat. No. 4,927,421; and to Bowman, et al, U.S. Pat. No. 4,950,270. None of which interference devices, however, involves use of a transverse pin like that of the invention whereover a tendon or ligament is looped over the pin set across the tunnel for both tendon positioning and as an endosteal mounting.

Within the knowledge of the inventors, in a practice of an arthroscopic surgical procedure on a patient's knee, no device has heretofore addressed the need for conveniently fitting a tendon, or the like, into a closed femoral tunnel section of a straight ligament tunnel and securing it by fitting a transverse pin therein like the tendon threader and process for its use of the invention.

SUMMARY OF THE INVENTION

It is a principal object of the present invention in a tendon threader to provide a device for use in an arthroscopic knee surgical procedure for fitting a tendon, or suture secured to a tendon end, into a closed end of a tunnel section of a straight ligament tunnel.

Another object of the present invention in a tendon threader is to provide a device that is utilized by a surgeon who operates observing a fluoroscopic monitor to fit the tendon threader, mounting a tendon, or a suture secured to an end of a tendon, bent into a loop over the threader end, into the prepared femoral tunnel, and captures that ligament by fitting a pin through which tunnel to pass through the tendon or suture loop.

Another object of the present invention is to provide for visualization of the transverse pin placement arthroscopically by fitting an arthroscope into the tendon threader end for verifying correct placement of the pin through the loop formed by the tendon and attached suture.

Still another object of the present invention is to provide a process that utilizes a tendon threader for installing a tendon into a closed end of a ligament tunnel, providing a tendon bent into a loop over which tendon threader, for receiving a pin fitted transversely through the tunnel and tendon loop permanently mounting the tendon; with an end of which tendon then pulled over the pin to where the tendon ends are aligned and are then secured under tension, as by stapling them onto the bone surface adjacent to the straight tunnel end.

Still another object of the present invention is to provide a device that is convenient and easy to use in a process for exactly positioning and mounting a tendon within a closed end of a femoral section of a straight ligament tunnel.

The present invention is in a device for fitting a tendon, or a suture that is connected onto a tendon end, and is bent across the device into a loop for fitting within a closed femoral end of a prepared straight ligament tunnel in a ligament replacement arthroscopic knee surgical procedure. Which surgical procedure is preferable performed by a surgeon who observes the operation on a fluoroscopic monitor or who visualizes it directly utilizing an arthroscope placed inside of the device.

As observed on the fluoroscopic or from the arthroscope, the surgeon both fits the tendon threader of the invention, that supports the tendon or suture secured to an end of a tendon mounted across the tendon threader forming a loop, through the tibial tunnel end, across the knee, and into the closed femoral tunnel section. When the surgeon determines the tendon or suture loop on the end of the tendon threader is appropriately positioned in the femoral tunnel section, he fits a pin through the side of the patient's knee so as to intersect that femoral tunnel section, the pin passing transversely thereacross and through the tendon or suture loop. Pulling the one tendon or suture end provides for sliding the tendon across the pin to where the tendon ends are aligned beyond the tibial tunnel end for securing, under tension, onto the bone surface adjacent to which tunnel end, completing the tendon installation.

The tendon threader of the invention, for use as set out above, includes a long shaft, that is preferably a tube, that mounts a collar on one end that can serve as a hand grip or may be utilized as a female coupling connector to accept a standard arthroscope, without a sheath, and contains a diaphragm or seal to prevent leakage of irrigation solution. The opposite tube end includes a pair of aligned wide longitudinal slots formed therein, with the remainder portions of the tube end adjacent to which wide slots each having a small longitudinal slot formed therein. Which small slots align, and are at right angles to the wide slots. The small slots are each to receive a tendon, or a suture that is connected to a tendon end, as by sewing. The suture or tendon is fitted in which small slots, forming a loop that extends across the tube end. The ends of which tendon, or suture secured to a tendon end, extend and are maintained along the tube side by the surgeon who fits the tube slotted end into the tibial end of the prepared ligament tunnel. The surgeon, observing the straight tunnel in a fluoroscopic or utilizing an arthroscope, guides the tube end to a mounting point as he selects in the femoral section of the straight ligament tunnel. When in use, the arthroscope is placed into the tendon threader to visualize the slotted end and looped tendon and observe the transverse pin passing through the tendon loop. When appropriately positioned with the tube end aligned wide slots opposite to a point in the tunnel wall through which the surgeon turns a pin, the pin passing transversely through the loop in the tendon or suture. The transverse pin thereby captures the suture or tendon, allowing the tendon threader to be removed, and the tendon or suture to be pulled over the pin. The tendon ends are aligned for mounting, as by stapling, onto the bone surface adjacent to the tibial tunnel end.

DESCRIPTION OF THE DRAWINGS

In the drawings that illustrate that which is presently regarded as the best mode for carrying out the invention:

FIG. 1 is a side elevation perspective view of a tendon threader of the invention showing a suture that is connected onto the end of a tendon, bent into a loop across small longitudinal slots formed in the end of a tube body;

FIG. 2 is side elevation perspective view like that of FIG. 1 only showing the tendon threader rotated through one hundred eighty (180) degrees, showing the interior of a collar end of which tube body into which an arthroscope may be inserted;

FIG. 3 is an expanded end perspective view of the collar end of the tube body shown removed in which an arthroscope, shown as a section of a lens and a diaphragm may be housed;

FIG. 4 is an expanded end perspective view of the tube body suture mounting end, showing a suture bent into a loop across the tube end small longitudinal slots, and showing a pin fitted through aligned wide longitudinal slots formed in the tube body end, the pin shown as having passed transversely through the suture loop;

DETAILED DESCRIPTION

Figure 5:
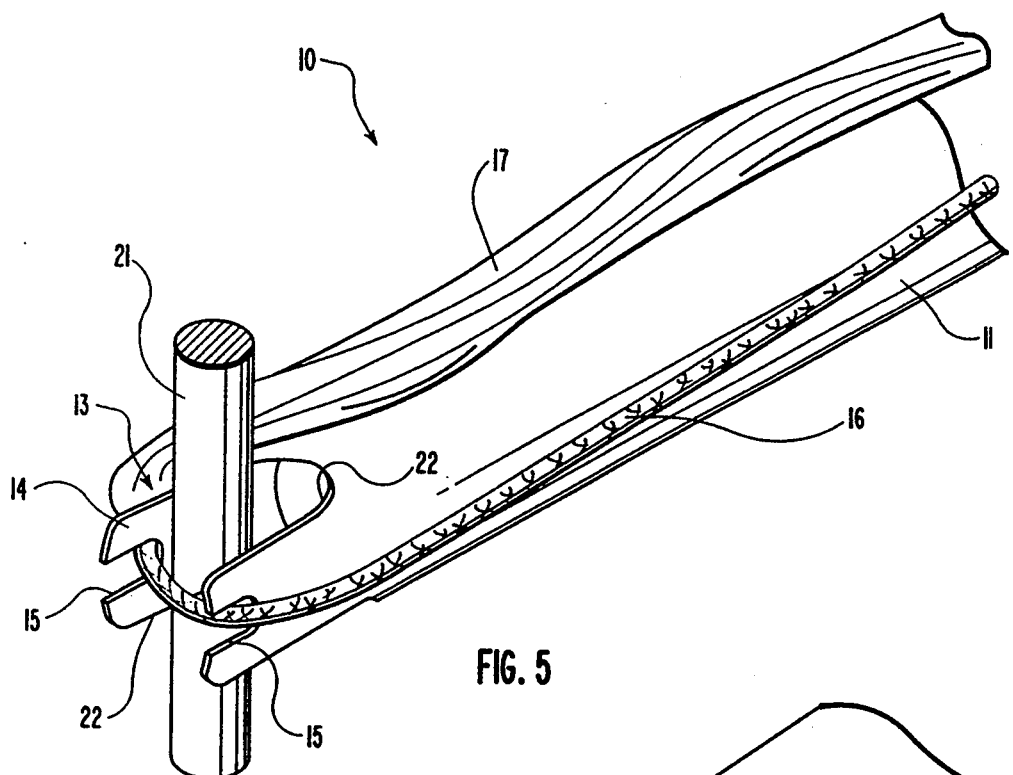
FIG. 5 is a expanded side elevation perspective view of the tube body mounting end, showing, the suture mounting slots enlarged for accommodating a tendon bent into a loop thereover.

A tendon threader 10 of the invention is shown in FIG. 1 as preferably consisting of a straight tube body 11 that mounts a collar 12 on one end. The tube body and collar are formed from a stiff material, such as stainless steel, that is suitable for use in a knee arthroscopic surgical procedure and, for re-use, can be sterilized in a conventional sterilization system. The other tube body end is show as formed with a pair of aligned wide notches or slots 13, leaving aligned remainder portions or tabs 14 that extend outwardly as tube end extensions. Each remainder portion or tab 14 is shown with a small suture slot 15 formed therein. The suture slots 15 are each for receiving and maintaining a suture 16 that is bent into a loop thereacross, and a suture is shown at 18 sewn onto the end of a tendon 17.

FIG. 2 shows the tendon threader 10 as having been rotated one hundred eighty (180) degrees, so as to position the collar 12 on top with the suture mounting end consisting of wide slots 13 and small suture slots 15 as the bottom end. The collar 12 is shown in FIG. 2 and in the expanded view of FIG. 3, to have a smooth inner wall 19, and is secured to the tube body 11 end at approximately a collar mid-point. As shown, the tube body end 20 constitutes a step between the collar interior surface and the tube body interior wall, which step, as shown in the exploded view of FIG. 3, may serve as a seat for a diaphragm 40 maintained thereagainst by the lens 41 end, shown as a lens section, of an arthroscope fitted in which collar 12. Which arthroscope lens 41 end can also include a gasket 42 fitted therearound for providing a friction coupling within which collar 12. The collar 12 may also serve as a handle for manipulation by a surgeon who utilizes the tendon threader in a knee arthroscopic surgical procedure, as set out later herein. The collar 12, used as a sleeve coupling for receiving the arthroscope 41 that includes the diaphragm 40 and/or seal 42, to prevent fluid leakage. Collar 12 could also serve as a coupling for joining another tube body, not shown, as a tube body extension, within the scope of this disclosure.

FIG. 4 shows an expanded view of the suture mounting end of the tendon threader with a suture 16 fitted across the tube end in the small slots 15 of the remainder tabs 14, and shows the suture bent into a loop across the tube end. Also shown therein, a section of a pin 21 has been fitted transversely through the ligament tunnel and has passed through the wide slots 13, and traveled through the suture loop. So arranged, pulling the tendon threader 10 away from the pin 21 moves the suture 16 into engagement with the surface of pin 21, sliding it out of the small slots 15, the pin anchoring the suture loop in the tunnel section.

FIG. 5 shows another embodiment of the tendon threader that is like the tendon threader 10 except that the small slots as shown as having been enlarged to large slots 22 that each have a cross section for accommodating the tendon 17 fitted across the tube body end and bent into a loop. Like FIG. 4, pin 21 is shown fitted transversely across the tendon threader of FIG. 5, passing through the wide slots 13 and through the loop formed in tendon 17 across the large slots 22. Like the arrangement, of FIG. 4, with the pin 21 installed across a femoral end of a straight ligament tunnel 33, as shown in FIG. 6, the tendon threader 10 can be withdrawn from the ligament tunnel and the tendon pulled out of the large slots 22 leaving it folded over the pin 21 surface.

Figure 6:
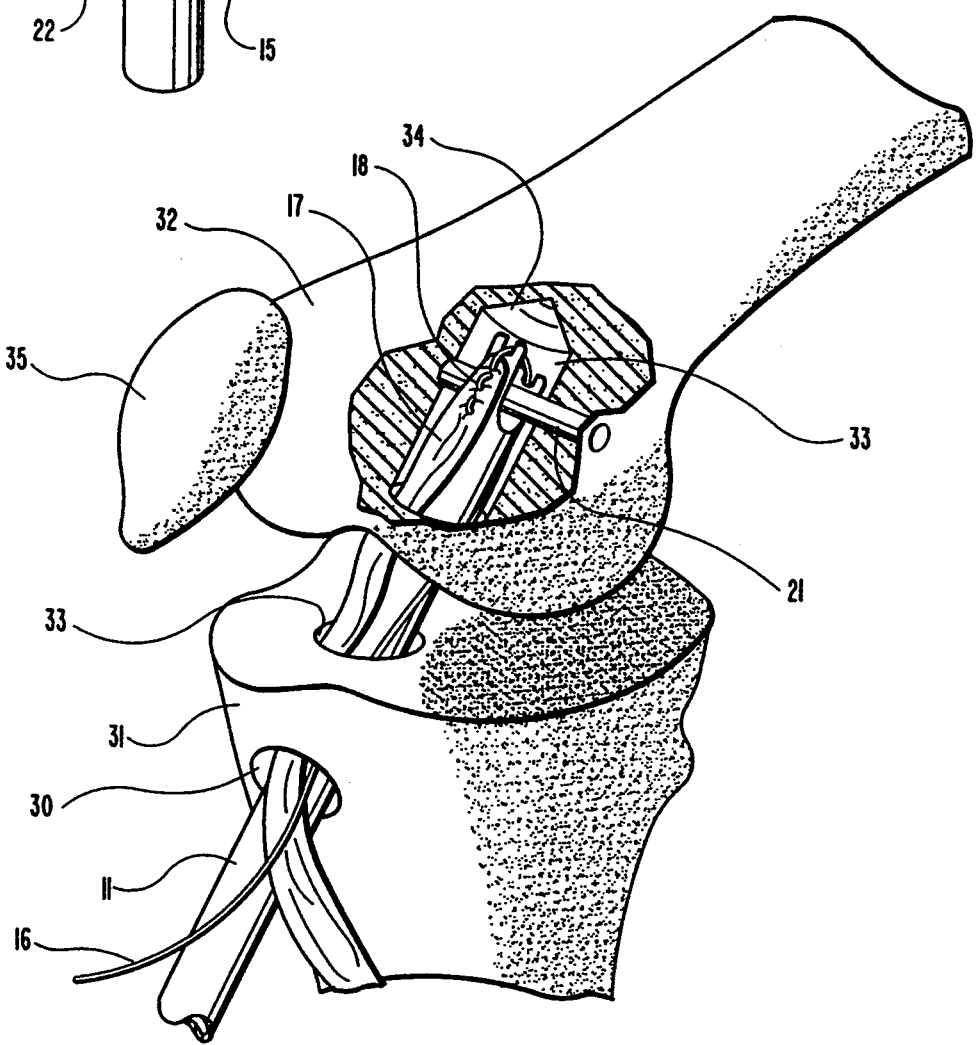
FIG. 6 is a side elevation perspective view of a patient's knee that has been bent appropriately for forming a straight ligament tunnel through the proximal tibia, extending across the ligament points of origin and into the distal femur endosteum, showing the tendon mounting end of the tendon threader tube body mounting a suture that is sewn to a tendon end fitted into the straight tunnel to the femur endosteum, and showing a pin passed transversely through the distal femur, across the femur tunnel section and through the tendon threader wide slots and the suture loop.

FIG. 6 illustrates a utilization of the tendon threader 10 of the invention fitted into a prepared straight ligament tunnel 33, and showing pin 21 fitted transversely across a femoral tunnel section 34. The pin 21 is shown as having passed through a suture 16 loop for positioning and mounting the tendon 17 in the tunnel section 34. The straight ligament tunnel 33 is shown formed from an opening 30 at the tibial tuberosity of the proximal tibia 31, passing through the anterior cruciate ligament points of origin in the knee joint and into the distal femur 32, and terminates in the femur endosteum at 34. Which ligament tunnel 33 formation and pin 21 installation procedures are accomplished without displacing the patella 35.

In practice, the tendon threader 10, with a suture 16 fitted across the small slots 15 that are formed in the remainder tabs 14 of the tube body 11, is slid into the straight ligament tunnel 33 by a surgeon observing the patient's knee on a fluoroscopic monitor, or by utilizing an arthroscope, or the like. The surgeon, as illustrated in FIG. 6, slides the tendon threader suture mounting end within the straight ligament tunnel to where it is located near to the femoral tunnel section 34 end in the femur endosteum. The arthroscope 41 can be fitted into the tendon threader, as illustrated in FIG. 3, to see the tunnel section end and observe the passage of pin 21 across the tunnel section. The surgeon positions the tendon threader to where the aligned wide slots 13 are opposite to a point in the tunnel wall where a drill is to be turned to. The pin 21 is turned into the knee to pass across the femoral tunnel section and through the loop formed in the suture 16. With the pin 21 mounted in the femoral tunnel section, as shown, the tendon threader 10 can then be withdrawn, with the suture 16 remaining looped or folded over pin 21. Thereafter, the surgeon can pull on the suture end so as to pull the attached tendon 17 over the pin to the attitude shown in FIG. 7.

Figure 7:
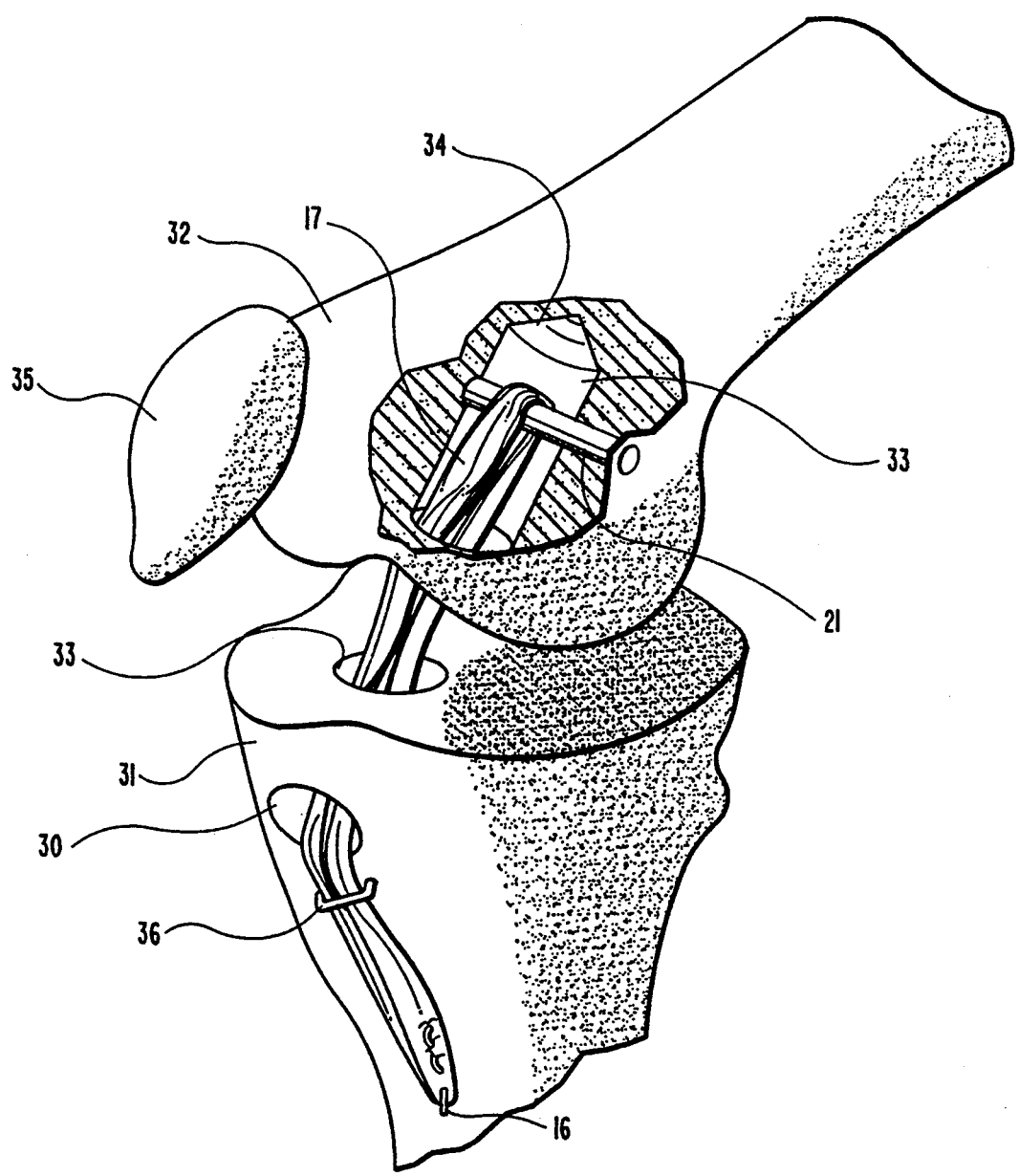
FIG. 7 is a view like that of FIG. 6 only showing the tendon threader as having been removed and the tendon pulled across the transverse pin to where the tendon ends are positioned above a point on the tibia cortex where they can be attached by a suitable technique, with one such technique shown as a staple spanning the tendon ends for hammering therein.

FIG. 7 shows the tendon 17 end that is attached to the suture end at 18, as by sewing, having been pulled out from the tibial open end 30 of the straight ligament tunnel. The two tendon 17 ends are shown as aligned and positioned at a point on the tibial cortex surface, adjacent to tibial tuberosity opening 30. A staple 36 is shown straddling which tendon ends and driven into the tibial cortex, the staple web to sandwich the tendon end surfaces against the tibial cortex surface. Prior to which staple mounting, a desired tensile force is applied to the tendon 17 that is anchored by the pin 21 in the femur endosteum. Whereafter, the tendon ends are stapled to the bone surface and the tendon ends below which staple 36 are removed, completing the tendon 17 mounting. It should, of course, be understood that another arrangement for anchoring tendon 17 to the tibial cortex surface could be employed within the scope of this disclosure.

While preferred embodiments of our invention in a tendon threader and process for its use for fitting a tendon into a prepared straight ligament tunnel as a anterior cruciate replacement, and endosteally mounting it therein have been shown and described herein, it should, however, be understood that this disclosure is made by way of example only and that variations to the invention as described are possible within the scope of this disclosure without departing from the subject matter coming within the scope of the following claims and a reasonable equivalency thereof, which claims we regard as our invention.

We claim:

1. A surgical method for endosteally mounting a tendon within a closed femoral tunnel section end of a straight ligament tunnel comprising the steps of, forming a tunnel into a patient's bent knee by arthroscopic procedure, employing a straight tube having a tendon mounting end including a pair of wide longitudinal slots forming aligned tube sections and each said tube section has a means formed on an upper end thereof for receipt of a tendon or a suture attached to a tendon end;

inserting said straight tube into a closed femoral tunnel section and positioning the suture or tendon in each of said notches in said tube sections to form a loop to receive a pin;

directing a pin through the side of the patient's knee so as to pass into said femoral tunnel section through said wide longitudinal slots and said loop;

removing said straight tube out from the straight ligament tunnel leaving said tendon or suture looped over the pin;

pulling one tendon or suture end to slide said tendon across said pin and out from said straight ligament tunnel to align said tendon ends over a mounting point on a tibial cortex adjacent the straight ligament tunnel;

applying a predetermined tensile force to said tendon and mounting said tendon ends to said mounting point on the tibial cortex.

2. A surgical method as recited in claim 1, wherein the surgeon observes the straight tube tendon mounting end insertion into the patient's knee on a fluroscopic monitor.

3. A surgical method as recited in claim 1 wherein the straight tube handle end includes a collar providing a gripping surface for the surgeon; and the tendon mounting end includes a pair of wide longitudinal slots formed in the tube end that align with one another to accommodate the pin passed therethrough, and the tendon or suture is maintained in small longitudinal slots that are means formed on each tube section upper end and are in said tube end remainder portions adjacent to said wide slots.

4. A surgical method as recited in claim 3, wherein the collar receives an arthroscope fitted therein to visualize the passing of the pin across the femoral tunnel through the tendon or suture loop.

5. A surgical method as recited in claim 1, wherein the tendon ends are mounted to the mounting point on the tibial cortex by a fixation device.

6. A surgical method as recited in claim 1, wherein fixation device for mounting the aligned tendon ends onto the tibial cortex is a staple having parallel legs with a web therebetween positioned over said tendon, said staple legs to straddle said tendon, and said staple legs are driven into the bone cortex to where said staple web compresses said tendon against said tibial cortex surface.

* * * * *